United States Patent [19]

Ogawa et al.

[11] Patent Number: 5,370,115
[45] Date of Patent: Dec. 6, 1994

[54] BIO-ELECTRODE AND METHOD OF PRODUCING THEREOF

[75] Inventors: Keikitsu Ogawa; Takashi Nakajima, both of Tokyo, Japan

[73] Assignee: Nihon Kohden Corporation, Tokyo, Japan

[21] Appl. No.: 32,551

[22] Filed: Mar. 17, 1993

[30] Foreign Application Priority Data

Mar. 17, 1992 [JP] Japan .................................. 4-58596

[51] Int. Cl.⁵ .............................................. A61B 5/04
[52] U.S. Cl. .................................. 128/639; 128/640; 607/152
[58] Field of Search ............... 128/639, 640, 641, 647; 607/152, 149, 153; 252/500

[56] References Cited

U.S. PATENT DOCUMENTS

| | | |
|---|---|---|
| 3,072,509 | 1/1963 | Barnhart et al. . |
| 3,108,917 | 10/1963 | McIrvine . |
| 3,265,638 | 8/1966 | Goodman et al. . |
| 3,301,723 | 1/1967 | Chrisp . |
| 3,658,726 | 4/1972 | Mühl . |
| 3,989,035 | 11/1976 | Zuehlsdorff ........................ 128/641 |
| 3,989,050 | 11/1976 | Buchalter . |
| 3,998,215 | 12/1976 | Anderson . |
| 4,016,869 | 4/1977 | Reichenberger . |
| 4,125,110 | 11/1978 | Hymes . |
| 4,299,231 | 11/1981 | Karmann et al. . |
| 4,362,165 | 12/1982 | Carmon et al. ...................... 128/640 |
| 4,406,827 | 9/1983 | Carim . |
| 4,692,273 | 9/1987 | Lawrence ........................... 252/500 |
| 4,947,847 | 8/1990 | Nakao et al. ...................... 252/500 |

FOREIGN PATENT DOCUMENTS 54-39385  3/1979  Japan .
1-58980  12/1989  Japan .

*Primary Examiner*—William E. Kamm
*Assistant Examiner*—Buc M. Green
*Attorney, Agent, or Firm*—Sughrue, Mion, Zinn, Macpeak & Seas

[57] ABSTRACT

Disclosure is a bio-electrode which can prevent paste from oozing out and color change from occurring and which allows the measurement to be stably performed even at the time immediately after the application. A catalyst is injected into sponge in a foam tape and then a monomer is injected into the sponge. Thereafter, paste is injected into a center portion of a surface of the sponge which is in the side opposite to an electrode element.

4 Claims, 1 Drawing Sheet

BIO-ELECTRODE AND METHOD OF PRODUCING THEREOF

BACKGROUND OF INVENTION

This invention relates to a method of producing a bio-electrode which is used in a measurement for obtaining an electrocardiograph or the like and applied to the skin.

A conventional bio-electrode of such a kind is produced as shown in FIG. 2. In FIG. 2, a label 2 is stuck on one surface of a flat foam tape 1. Then, paint 5 of Ag or AgCl powder in which an ABS resin is used as a binder is applied to the surface which is in the side opposite to a projection 4a of an electrode element 4. A small hole 3 is formed at the center portion of the label 2, and the projection 4a of the electrode element 4 is inserted into the small hole 3 so that the electrode element 4 is attached to the label 2. Thereafter, sponge 6 is inserted into the foam tape 1, a catalyst such as boric acid or a borate solution is injected into the sponge 6, and a monomer such as a polyvinyl alcohol solution is then injected into the sponge. As a result of these procedures, the existence of the catalyst causes the hardness of the monomer to gradually increase so that a state where the sponge 6 is impregnated with solid gel is obtained. Finally, the sponge 6 is covered by a plastic cover 7. Instead of impregnating the sponge 6 with solid gel, the sponge 6 may be impregnated with paste.

Since paste is not used in sponge impregnated with solid gel, the sponge is not sticky. After the sponge is peeled from a skin, therefore, it is not required to wipe off a sticky substance. However, the nonuse of paste and the low water content of the sponge cause a problem to arise that the electric skin resistance is so high that it requires a long period to drop to a low level. This causes a drift or a polarization voltage to be generated until the electric skin resistance becomes stable in level, whereby the measurement may be adversely affected.

By contrast, in sponge impregnated with the paste, the use of paste makes the electric skin resistance low and hence the electric skin resistance drops to a low level in a short period. This allows the measurement to be stably performed immediately after the application of a bio-electrode. When the cover 7 is pressed during storage of a bio-electrode, however, paste oozes out from the adhesive interface between the foam tape and the cover so that the surroundings are stained with the paste.

SUMMARY OF THE INVENTION

The invention has been conducted in view of the above-mentioned circumstances. It is an object of the invention to provide a method of producing a bio-electrode which can prevent paste from oozing out and which allows the measurement to be stably performed even at the time immediately after the application.

In order to attain the object, the method of producing a bio-electrode, in which a hole is formed at a center portion of a label adhering to one surface of a flat foam tape, a projection of an electrode element is inserted into the hole, and sponge is inserted into the foam tape to be stuck on the electrode element, comprises the steps of: injecting a catalyst into the sponge and then injecting a monomer into the sponge to form a gel; and injecting paste into a center portion of a surface of the sponge, the surface being in the side opposite to the electrode element.

According to the above-mentioned method, paste is used so that the electric skin resistance is low and drops to a low level in a short period. Moreover, the placement of sponge impregnated with solid gel between the paste and the label prevents the paste from oozing toward the side of the label. Therefore, the paste does not ooze out during storage of a bio-electrode.

DETAILED DESCRIPTION OF THE PREFERRED EMBODIMENTS

Hereinafter, an embodiment of the method of producing a bio-electrode according to the invention will be described with reference to the drawings.

Figure 1:
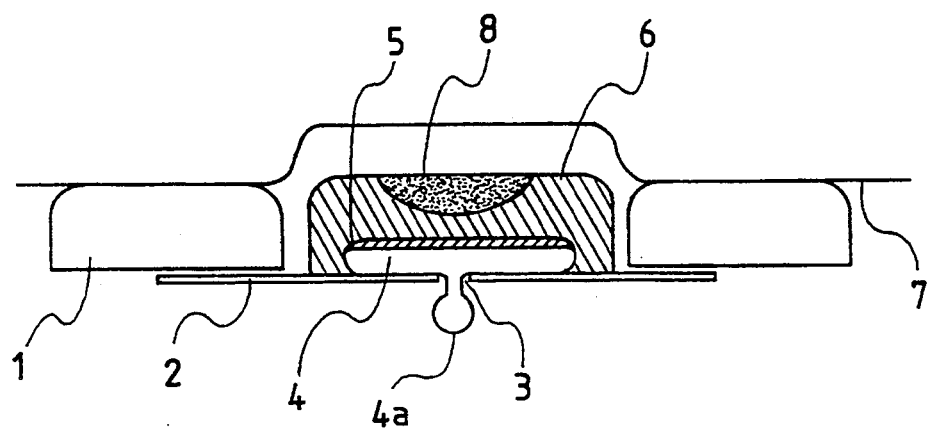
FIG. 1 is a longitudinal sectional view showing the configuration of a bio-electrode produced by an embodiment of the production method of the invention.
Figure 2:
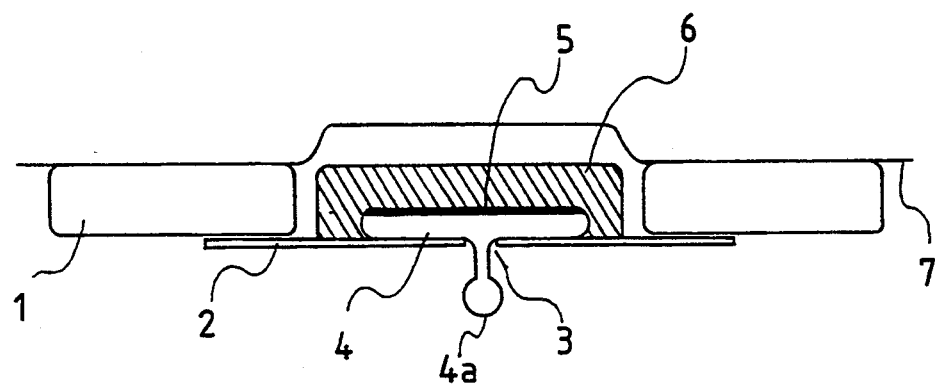
FIG. 2 is a longitudinal sectional view showing the configuration of a bio-electrode produced by a conventional production method.

FIG. 1 shows the configuration of a bio-electrode produced by the embodiment. In FIG. 1, portions corresponding to those of the conventional example of FIG. 2 are designated by the same reference numerals, and their description is omitted. Initially, paint 5 of Ag or AgCl powder in which an ABS resin is used as a binder is applied to the surface which is in the side opposite to a projection 4a of an electrode element 4. Then, a label 2 is stuck on one surface of a foam tape 1, and a small hole 3 is formed at the center portion of the label 2. The projection 4a of the electrode element 4 is inserted into the small hole 3 so that the electrode element 4 is attached to the label 2. Thereafter, sponge 6 is inserted into the foam tape 1, a catalyst such as boric acid or a borate solution is injected into the sponge 6, and a monomer such as a polyvinyl alcohol solution is then injected into the sponge 6. Immediately after this injection of the monomer, the monomer begins to harden and the hardening completes within several seconds so as to obtain elastic solid gel. After that, following the injection of the monomer, injected into a center portion of the sponge 6, thereby forming a paste-impregnated portion 8. Finally, the sponge 6 is covered by a plastic cover 7. The paste of the present invention corresponds to an aqueous mixture including a conductive salt such as sodium chloride. The aqueous mixture has a viscosity being higher than 20,000 cP (centipoise), more preferably, 27,000–32,000 cP.

According to the embodiment, the sponge 6 is partly impregnated with paste, and therefore the electric skin resistance is low so as to drop to a low level in a short period, thereby allowing the measurement to be stably performed even at the time immediately after the application. Furthermore, since the sponge 6 impregnated with solid gel exists between the paste-impregnated portion 8 and the label 2, even when the cover 7 is pressed during storage of the bio-electrode, paste is prevented from oozing out so that the product value is not impaired.

As described above, according to the method of producing a bio-electrode of the invention, paste is injected into a portion of sponge which has been subjected to solid gelation, and therefore the paste is prevented from oozing out and the measurement can be stably performed even at the time immediately after the application of the bio-electrode.

What is claimed is:

1. A method of producing a bio-electrode comprising the steps of:
   forming a hole at a center portion of a label adhering to one surface of a flat foam tape;
   inserting a projection of an electrode element into said hole;
   inserting a sponge into a cavity in said foam tape, said sponge to be adhered to said electrode element;
   injecting a catalyst into said sponge and then injecting a monomer into said sponge to form a gel; and
   injecting high-viscosity paste into a center portion of a surface of said sponge, said sponge surface being in the side opposite to said electrode element.

2. A bio-electrode as claimed in claim 1, wherein said paste has a viscosity in a range between 27,000–32,000 cP.

3. A bio-electrode comprising:
   a label having a hole formed at a center portion thereof;
   a flat foam tape, said label adhering to one surface of said flat foam tape;
   an electrode element having a projection which is inserted into the hole;
   sponge inserted into a cavity in the foam tape to be stuck on the electrode element, a catalyst injected into said sponge and a monomer injected into said sponge to form a gel; and
   paste injected into a center portion of a surface of said sponge, said surface being in the side opposite to the electrode element.

4. A bio-electrode as claimed in claim 3, wherein said paste has a viscosity in a range between 27,000–32,000 cP.

* * * * *